(12) United States Patent
Mailliet et al.

(10) Patent No.: US 8,034,939 B2
(45) Date of Patent: Oct. 11, 2011

(54) ISOINDOLE DERIVATIVES, COMPOSITIONS CONTAINING SAME, PREPARATION THEREOF AND PHARMACEUTICAL USES THEREOF IN PARTICULAR AS INHIBITORS OF CHAPERONE PROTEIN HSP90 ACTIVITIES

(75) Inventors: Patrick Mailliet, Fontenay Sous Bois (FR); Luc Bertin, Crosnes (FR); Didier Benard, Montsoult (FR); Chantal Carrez, Thiais (FR); François Vallee, Meudon (FR); Eric Bacque, Gif sur Yvette (FR)

(73) Assignee: Aventis Pharma S.A.., Antony (FR)

( * ) Notice: Subject to any disclaimer, the term of this patent is extended or adjusted under 35 U.S.C. 154(b) by 932 days.

(21) Appl. No.: 11/864,105

(22) Filed: Sep. 28, 2007

(65) Prior Publication Data

US 2008/0119507 A1    May 22, 2008

Related U.S. Application Data

(63) Continuation of application No. PCT/FR2006/000750, filed on Apr. 5, 2006.

(30) Foreign Application Priority Data

Apr. 8, 2005    (FR) ..................... 05 03511

(51) Int. Cl.
  *C07D 221/04*    (2006.01)
  *A61K 31/437*    (2006.01)
(52) U.S. Cl. .......................... 546/79; 514/290
(58) Field of Classification Search ............. 546/79; 514/290
  See application file for complete search history.

(56) References Cited

U.S. PATENT DOCUMENTS

2007/0032532 A1    2/2007    Nara et al.

FOREIGN PATENT DOCUMENTS

| WO | WO 2004/050087 A1 | 6/2004 |
|---|---|---|
| WO | WO 2004/056782 A1 | 7/2004 |
| WO | WO 2004/072051 A1 | 8/2004 |
| WO | WO 2004/072080 A1 | 8/2004 |
| WO | WO 2004/096212 A1 | 11/2004 |
| WO | WO 2005/000300 A1 | 1/2005 |
| WO | WO 2005/000778 A1 | 1/2005 |

OTHER PUBLICATIONS

Dorwald F. A. Side Reactions in Organic Synthesis, 2005, Wiley: VCH, Weinheim p. IX of Preface.*

Chiosis et al, A Small Molecuule Designed to Bind to the Adenine Nucleotide Pocket of Hsp90 Causes Her2 Degradation and the Growth Arrest and Differentiation of Breast Cancer Cells, Chemistry & Biology; 8 (2001) pp. 289-299.

Chiosis et al, Development of Purine-Scaffold Small Molecule Inhibitors of HSP90, Current Cancer Drug Targets, 2003, 3, pp. 371-376.

* cited by examiner

*Primary Examiner* — Rita Desai
(74) *Attorney, Agent, or Firm* — Scully, Scott, Murphy & Presser, P.C.

(57) ABSTRACT

This invention relates to isoindole derivates of Formula I to pharmaceutical compositions comprising such derivatives, and to methods of treatment comprising administering of such derivatives.

8 Claims, No Drawings

ISOINDOLE DERIVATIVES, COMPOSITIONS CONTAINING SAME, PREPARATION THEREOF AND PHARMACEUTICAL USES THEREOF IN PARTICULAR AS INHIBITORS OF CHAPERONE PROTEIN HSP90 ACTIVITIES

The present invention relates to novel chemical compounds which are isoindole derivatives, and also to compositions which contain them, and to the use thereof as medicinal products.

The present invention relates more particularly to the pharmaceutical uses thereof and in particular the use thereof as inhibitors of the activities of the Hsp90 chaperone protein.

Such derivatives according to the present invention can in particular be 1-(benzimidazol-2-yl)-2,3,4,6-tetrahydro-2H-pyrido[2,1-a]isoindole derivatives, 1-(azabenzimidazol-2-yl)-2,3,4,6-tetrahydro-2H-pyrido[2,1-a]isoindole derivatives, 1-(benzimidazol-2-yl)-2,5-dihydro-3H-pyrrolo[2,1-a]isoindole derivatives or 1-(azabenzimidazol-2-yl)-2,5-dihydro-3H-pyrrolo[2,1-a]isoindole derivatives.

The compounds according to the present invention exhibit especially an anticancer activity, and in particular an inhibitory activity on the Hsp90 chaperone protein, and more particularly via the inhibition of the ATPase-type catalytic activity of the Hsp90 chaperone protein.

Chaperone Proteins

Molecular chaperones of the "Heat Shock Proteins" family (HSPs), classified according to their molecular mass (Hsp27, Hsp70, Hsp90, etc.), are key elements in the balance between the synthesis and the degradation of the cellular proteins responsible for the correct folding of proteins. They play a vital role in response to cellular shock. HSPs, and in particular Hsp90, are also involved in the regulation of various major functions of the cell, via their association with various client proteins involved in cell proliferation or apoptosis (Jolly C. and Morimoto R. I., J. N. Cancer Inst.(2000), 92, 1564-72; Smith D. F. et al., Pharmacological Rev. (1998), 50, 493-513; Smith D. F., Molecular Chaperones in the Cell, 165-178, Oxford University Press 2001).

Various human pathologies result in incorrect folding of key proteins, resulting in particular in neurodegenerative diseases subsequent to the aggregation of certain proteins as in Alzheimer's diseases and Huntington's disease or prion-related diseases (Tytell M. and Hooper P. L., Emerging Ther. Targets (2001), 5, 267-287). In these pathologies, approaches aimed at breaking up or at disturbing the function of chaperones could be beneficial.

Hsp90 Chaperone

The Hsp90 chaperone, which represents 1 to 2% of the protein content of the cell, has recently been demonstrated as a particularly promising target in anticancer therapy (cf. for review: Moloney A. and Workman P., Expert Opin. Biol. Ther. (2002), 2(1), 3-24; Choisis et al, Drug Discovery Today (2004), 9, 881-888). This advantage comes in particular from the cytoplasmic interactions of Hsp90 with the main client proteins of Hsp90, which proteins are involved in the six mechanisms of tumour progression, as defined by Hanahan D. and Weinberg R. A. (Cell (2002), 100, 57-70), i.e.:
- an ability to proliferate in the absence of growth factors: EGFR-R/HER2, Src, Akt, Raf, MEK, Bcr-Abl, Flt-3, etc.,
- an ability to evade apoptosis: mutated form of p53, Akt, survivin, etc.,
- an insensitivity to proliferation stop signals: Cdk4, Plk, Wee1, etc.,
- an ability to activate angiogenesis: VEGF-R, FAK, HIF-1, Akt, etc.,
- an ability to proliferate with no replicative limit: hTert, etc.,
- an ability to invade new tissues and to metastasize: c-Met.

Among the other client proteins of Hsp90, steroid hormone receptors, such as the oestrogen receptor or the androgen receptor, also exhibit a considerable advantage in the context of anticancer therapies.

It has recently been shown that the alpha form of Hsp90 also has an extracellular role via its interaction with the MMP-2 metalloprotease, itself involved in tumour invasion (Eustace B. K. et al, Nature Cell Biology (2004), 6, 507-514).

Hsp90 comprises two N- and C-terminal domains separated by a highly charged region. The dynamic interaction between these two domains, coordinated by the binding of nucleotides and of cochaperones, determines the conformation of the chaperone and its activation state. The association of the client proteins depends mainly on the nature of the cochaperones Hsp70/Hsp40, Hop60 etc., and on the nature of the ADP or ATP nucleotide bound to the N-terminal domain of Hsp 90. Thus, the hydrolysis of ATP to ADP and the ADP/ATP exchange factor control all the chaperone "machinery", and it has been shown that it is sufficient to prevent the hydrolysis of ATP to ADP—ATPase activity of Hsp90—to release into the cytoplasm client proteins which will then be degraded in the proteasome (Neckers L and Neckers K, Expert Opin. Emerging Drugs (2002), 7, 277-288; Neckers L, Current Medicinal Chemistry, (2003), 10, 733-739; Piper P. W., Current Opin. Invest. New Drugs (2001), 2,1606-1610).

Hsp90 inhibitors

The first known inhibitors of Hsp90 are compounds of the ansamycin family, in particular geldanamycin (1) and herbimycin A. X-ray studies have shown that geldanamycin binds to the ATP site of the N-terminal domain of Hsp90, where it inhibits the ATPase activity of the chaperone (Prodromou C. et al, Cell (1997), 90, 65-75)

Currently, the NIH and Kosan BioSciences are carrying out the clinical development of 17AAG (2), which is an Hsp90 inhibitor derived from geldanamycin (1), which blocks the ATPase activity of Hsp 90 by binding to the N-terminal ATP recognition site. The results of the phase I clinical trials for 17AAG (2) today result in the initiation of phase II trials, but also direct research towards more soluble derivatives such as the analogue 3 (17DMAG from Kosan BioSciences), bearing a dimethylamino chain in place of the methoxy residue, and towards optimized formulations of 17AAG (CNF1010 from Conforma Therapeutics):

(1)

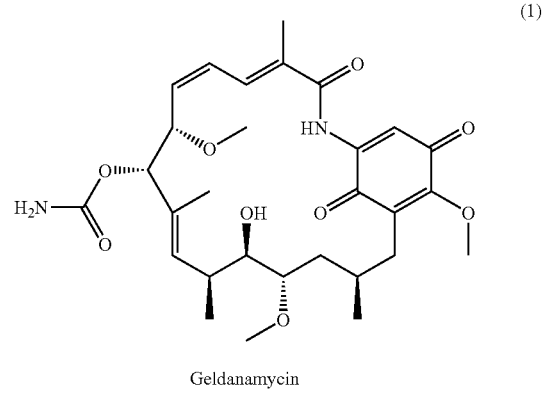

Geldanamycin (2)

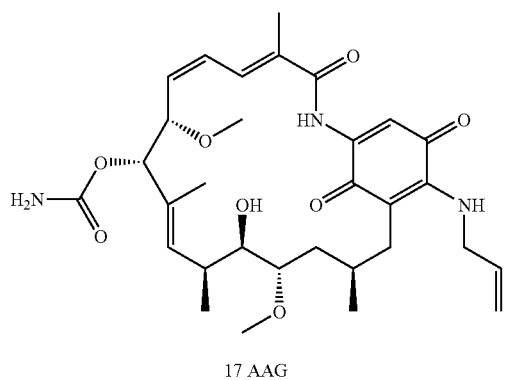

17 AAG (3)

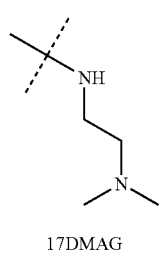

17DMAG

Radicicol (4) is also an Hsp90 inhibitor of natural origin (Roe S. M. et al, J. Med Chem. (1999), 42, 260-66). However, although the latter is by far the best in vitro inhibitor of Hsp90, its metabolic instability with respect to sulphur-containing nucleophiles makes it difficult to use in vivo. Oxime derivatives that are much more stable, such as KF 55823 (5) or KF 25706 have been developed by the company Kyowa Hakko Kogyo (Soga et al, Cancer Research (1999), 59, 2931-2938)

(4)

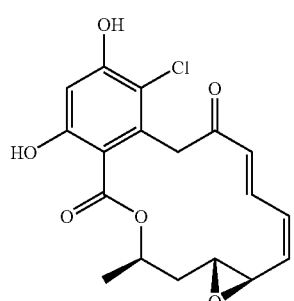

Radicicol (5)

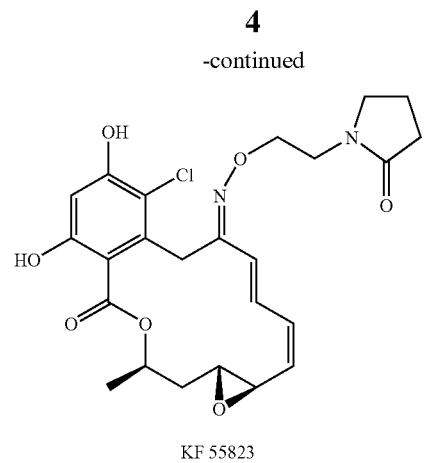

KF 55823

Structures of natural origin, related to radicicol, have also been recently described, such as zearalenone (6) by the company Conforma Therapeutics (WO 03041643) or the compounds (7-9).

(6)

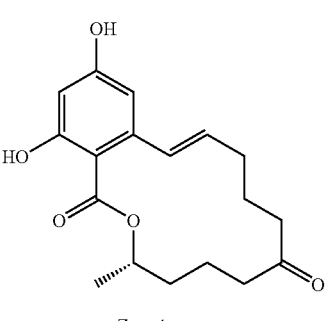

Zearalenone (7)

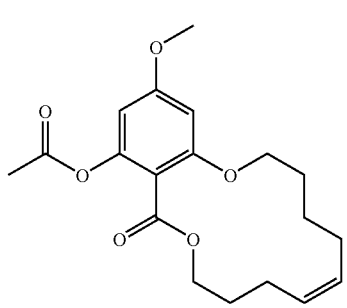

(8)

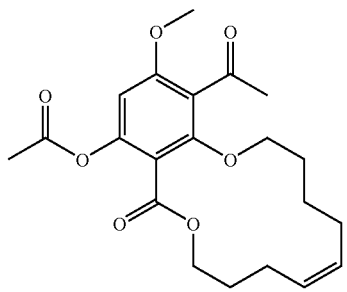

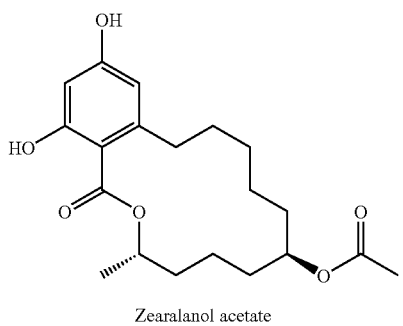

Zearalanol acetate

An Hsp90 inhibitor of natural origin, novobiocin (10) binds to a different ATP site located in the C-terminal domain of the protein (Itoh H. et al, Biochem J. (1999), 343, 697-703.

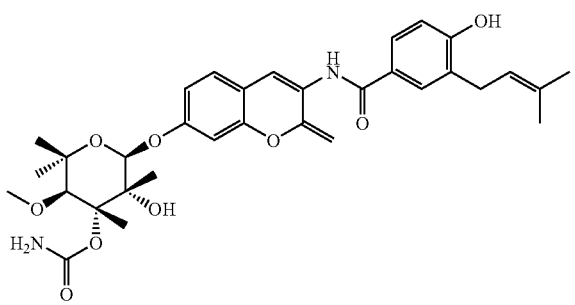

(10)

A depsipeptide, called pipalamycin or ICI101, has just been recently described as a noncompetitive inhibitor of the ATP site of Hsp90 (J. Pharmacol. Exp. Ther. (2004), 310, 1288-1295).

Purines, such as the compounds PU3 (11) (Chiosis et al, Chem. Biol. (2001), 8, 289-299) and PU24FCI (12) (Chiosis et al, Curr. Canc. Drug Targets (2003), 3, 371-376), have also been described as Hsp90 inhibitors:

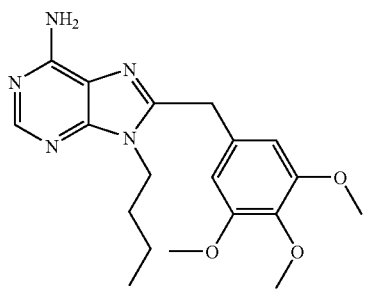

(11)

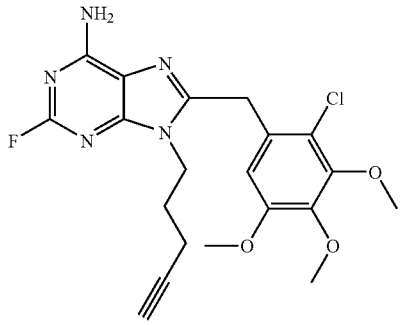

(12)

Patent application WO2004/072080 (Cellular Genomics) claims a family of 8-heteroaryl-6-phenylimidazo[1,2-a]pyrazines as Hsp90 activity modulators.

Patent application WO2004/050087 (Ribotarget/Vernalis) claims a family of pyrazoles that are useful for treating pathologies related to the inhibition of "Heat Shock Proteins" such as the Hsp90 chaperone.

Patent application WO2004/056782 (Vernalis) claims a novel family of pyrazoles that are useful for treating pathologies related to the inhibition of "Heat Shock Proteins" such as the Hsp90 chaperone.

Patent application WO2004/072051 (Vernalis) claims arylisoxazole derivatives that are useful for treating pathologies related to the inhibition of "Heat Shock Proteins" such as the Hsp90 chaperone.

Patent application WO2004/096212 (Vernalis) claims a third family of pyrazoles that are useful for treating pathologies related to the inhibition of "Heat Shock Proteins" such as the Hsp90 chaperone.

Patent application WO2005/00300 (Vernalis) claims more generally heterocycles with 5 ring members, substituted with aryl radicals, that are useful for treating pathologies related to the inhibition of "Heat Shock Proteins" such as the Hsp90 chaperone.

Finally, patent application WO2005/00778 (Kyowa Hakko Kogyo) claims a family of benzophenone derivatives as Hsp90 inhibitors that are useful for the treatment of tumours.

A subject of the present invention is thus the products of formula (I)

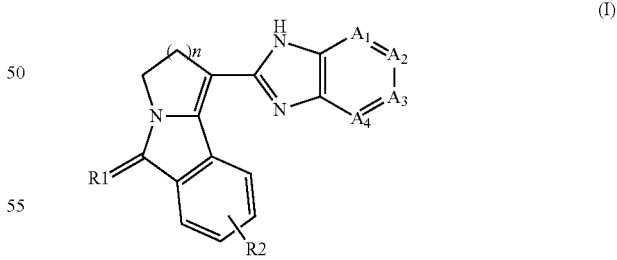

(I)

in which:
A1, A2, A3 and A4, which may be identical or different, are CRa or N;
n is the integer 1 or 2;
R1 is an oxygen or sulphur atom or a radical NRb;
R2 is independently selected from the group comprising H, halogen, CF3, nitro, cyano, methyl, ethyl, hydroxyl, mercapto, amino, methoxy, thiomethoxy, methylamino, dimethylamino, acetylamino, carboxyl and carboxamido;

Ra is selected from the group comprising H, halogen, CF3, hydroxyl, mercapto, nitro, amino, OR3, SR3, NR3R4, NH—OH, NH—CO—H, NH—CO—OH, NH—CO—NH2, carboxyl, cyano, carboxamido, Y—(CH$_2$)p-alkyl, Y—(CH$_2$)p-cycloalkyl, Y—(CH$_2$)p-heterocycloalkyl, Y—(CH$_2$)p-aryl or Y—(CH$_2$)p-heteroaryl, with Y=O, S, NH, O—C(O), C(O)—NH, NH—C(O), NH—S(O) or NH—S(O)2, with p=1, 2 or 3, and in which the aryl radical contains from 6 to 10 ring members, the cycloalkyl radical contains from 3 to 10 ring members and the heteroaryl or heterocycloalkyl radical contains from 4 to 10 ring members, including 1 to 3 hetero atoms chosen from O, N or S; all these radicals being optionally substituted, R3 and R4 are independently chosen from a hydrogen atom or alkyl, alkenyl, alkynyl, aryl, heteroaryl, aralkyl or heteroaralkyl radicals; all the alkyl, alkenyl, alkynyl, aryl, heteroaryl, aralkyl or heteroaralkyl radicals above are optionally substituted;

Rb is selected from the group comprising H, (CH$_2$)m-cycloalkyl, (CH$_2$)m-heterocycloalkyl, (CH$_2$)m-aryl or (CH$_2$)m-heteroaryl, with m=0, 1 or 2, all these radicals being optionally substituted, said products of formula (I) being in all the possible racemic, enantiomeric and diastereoisomeric isomer forms, and also the addition salts with inorganic and organic acids or with inorganic and organic bases of said products of formula (I).

In the products of formula (I) and below, the terms indicated have the meanings which follow:

the term "halogen" refers to fluorine, chlorine, bromine or iodine atoms, and preferably chlorine or bromine atoms;

the term "alkyl radical" refers to a linear or branched radical containing at most 12 carbon atoms, chosen from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl and tert-hexyl radicals and also heptyl, octyl, nonyl, decyl, undecyl and dodecyl radicals, and also the linear or branched positional isomers thereof. Mention is more particularly made of alkyl radicals containing at most 6 carbon atoms, and in particular methyl, ethyl, propyl, isopropyl, n-butyl, isobutyl, tert-butyl, linear or branched pentyl, linear or branched hexyl radicals;

the term "alkenyl radical" refers to a linear or branched radical containing at most 12 carbon atoms, and preferably 4 carbon atoms, chosen, for example, from the following values: ethenyl or vinyl, propenyl or allyl, 1-propenyl, n-butenyl, i-butenyl, 3-methylbut-2-enyl, n-pentenyl, hexenyl, heptenyl, octenyl, cyclohexylbutenyl and decenyl, and also the linear or branched positional isomers thereof. Among the alkenyl values, mention is made more particularly of the allyl or butenyl values;

the term "alkynyl radical" refers to a linear or branched radical containing at most 12 carbon atoms, and preferably 4 carbon atoms, chosen, for example, from the following values: ethynyl, propynyl or propargyl, butynyl, n-butynyl, i-butynyl, 3-methylbut-2-ynyl, pentynyl or hexynyl, and also the linear or branched positional isomers thereof. Among the alkynyl values, mention is more particularly made of the propargyl value;

the term "alkoxy radical", that can be represented for example by OR3, refers to a linear or branched radical containing at most 12 carbon atoms, and preferably 6 carbon atoms, chosen, for example, from methoxy, ethoxy, propoxy, isopropoxy, linear, secondary or tertiary butoxy, pentoxy, hexoxy or heptoxy radicals, and also the linear or branched positional isomers thereof;

the term "alkylthio" or "alkyl-S—", that can be represented for example by SR3, refers to a linear or branched radical containing at most 12 carbon atoms, and is in particular methylthio, ethylthio, isopropylthio and heptylthio radicals. In the radicals comprising a sulphur atom, the sulphur atom can be oxidized to an SO or S(O)2 radical;

the term "acryl radical" or "R—CO—" refers to a linear or branched radical containing at most 12 carbon atoms in which the radical r is a hydrogen atom, or an alkyl, cycloalkyl, cycloalkenyl, cycloalkyl, heterocycloalkyl or aryl radical, these radicals having the values indicated above and being optionally substituted as indicated: mention is, for example, made of formyl, acetyl, propionyl, butyryl or benzoyl radicals, or else valeryl, hexanoyl, acryloyl, crotonoyl or carbamoyl radicals;

the term "cycloalkyl radical" refers to a monocyclic or bicyclic carbocyclic radical containing from 3 to 10 ring members and refers in particular to cyclopropyl, cyclobutyl, cyclopentyl and cyclohexyl radicals;

the term "cycloalkylalkyl radical" refers to a radical in which cycloalkyl and alkyl are chosen from the values indicated above: this radical thus refers, for example, to cyclopropylmethyl, cyclopentylmethyl, cyclohexylmethyl and cycloheptylmethyl radicals;

the term "acyloxy radical" is intended to mean acyl-O— radicals in which acyl has the meaning indicated above: mention is, for example, made of acetoxy or propionyloxy radicals;

the term "acylamino radical" is intended to mean acyl-N— radicals in which acyl has the meaning indicated above;

the term "aryl radical" refers to unsaturated carbocyclic radicals that are monocyclic or comprise condensed rings. As examples of such an aryl radical, mention may be made of phenyl or naphthyl radicals: mention is more particularly made of the phenyl radical;

the term "arylalkyl" is intended to mean radicals resulting from combination of the alkyl radicals mentioned above, that are optionally substituted, and the aryl radicals also mentioned above, that are optionally substituted: mention is, for example, made of benzyl, phenylethyl, 2-phenethyl, triphenylmethyl or naphthalenemethyl radicals;

the term "heterocyclic radical" refers to a saturated (heterocycloalkyl) or unsaturated (heteroaryl) carbocyclic radical comprising at most 6 ring members interrupted with one or more identical or different hetero atoms chosen from oxygen, nitrogen or sulphur atoms.

As heterocycloalkyl radicals, mention may in particular be made of dioxolane, dioxane, dithiolane, thiooxolane, thiooxane, oxiranyl, oxolanyl, dioxolanyl, piperazinyl, piperidyl, pyrrolidinyl, imidazolidinyl, pyrazolidinyl, morpholinyl, tetrahydrofuryl, tetrahydrothienyl, chromanyl, dihydrobenzofuryl, indolinyl, piperidyl, perhydropyranyl, pyrindolinyl, tetrahydroquinolinyl, tetrahydroisoquinolinyl or thioazolidinyl radicals, all these radicals being optionally substituted.

Among the heterocycloalkyl radicals, mention may in particular be made of optionally substituted piperazinyl, optionally substituted piperidyl, optionally substituted pyrrolidinyl, imidazolidinyl, pyrazolidinyl, morpholinyl or thioazolidinyl radicals.

The term "heterocycloalkylalkyl radical" is intended to mean radicals in which the heterocycloalkyl and alkyl residues have the meanings above;

among the heteroaryl radicals with 5 ring members, mention may be made of furyl radicals, such as 2-furyl, thienyl radicals, such as 2-thienyl and 3-thienyl, and pyrrolyl, diazolyl, thiazolyl, thiadiazolyl, thiatriazolyl, isothiazolyl, oxazolyl, oxadiazolyl, 3- or 4-isoxazolyl, imidazolyl, pyrazolyl and isoxazolyl radicals.

Among the heteroaryl radicals with 6 ring members, mention may in particular be made of pyridyl radicals such as 2-pyridyl, 3-pyridyl and 4-pyridyl and pyrimidyl, pyrimidinyl, pyridazinyl, pyrazinyl and tetrazolyl radicals.

As condensed heteroaryl radicals containing at least one hetero atom chosen from sulphur, nitrogen and oxygen, mention may, for example, be made of benzothienyl such as 3-benzothienyl, benzofuryl, benzofuranyl, benzopyrrolyl, benzimidazolyl, benzoxazolyl, thionaphthyl, indolyl, purinyl, quinolinyl, isoquinolinyl and naphthyridinyl.

Among the condensed heteroaryl radicals, mention may more particularly be made of benzothienyl, benzofuranyl, indolyl or quinolinyl, benzimidazolyl, benzothiazolyl, furyl, imidazolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, 1,3,4-thiadiazolyl, thiazolyl and thienyl radicals and triazolyl groups, these radicals being optionally substituted as indicated for the heteroaryl radicals.

the term "cyclic amine" that can be represented, for example, by NR3R4, refers to a cycloalkyl radical containing from 3 to 8 ring members in which a carbon atoms is replaced with a nitrogen atom, the cycloalkyl radical having the meaning indicated above and also possibly containing one or more other hetero atoms chosen from O, S, SO$_2$, N or NR3 with R3 as defined above; as examples of such cyclic amines, mention may, for example, be made of pyrrolidinyl, piperidyl, morpholinyl, piperazinyl, indolinyl, pyrindolinyl or tetrahydroquinolinyl radicals.

The term "patient" refers to human beings but also the other mammals.

The term "prodrug" refers to a product that can be converted in vivo by metabolic mechanisms (such as hydrolysis) into a product of formula (I). For example, an ester of a product of formula (I) containing a hydroxyl group can be converted by hydrolysis in vivo into its mother molecule. Alternatively, an ester of a product of formula (I) containing a carboxyl group can be converted by hydrolysis in vivo into its mother molecule.

By way of example, mention may be made of esters of products of formula (I) containing a hydroxyl group such as acetates, citrates, lactates, tartrates, malonates, oxalates, salicylates, propionates, succinates, fumarates, maleates, methylene-bis-b-hydroxynaphthoates, gentisates, isethionates, di-p-toluyl-tartrates, methanesulphonates, ethanesulphonates, benzenesulphonates, p-toluene-sulphonates, cyclohexylsulphamates and quinates.

Particularly useful esters of products of formula (I) containing a hydroxyl group can be prepared from acid residues such as those described by Bundgaard et. al., J. Med. Chem., 1989, 32, page 2503-2507: these esters include in particular substituted (aminomethyl)benzoates, dialkylaminomethylbenzoates in which the two alkyl groups can be linked together or can be interrupted with an oxygen atom or with an optionally substituted nitrogen atom or an alkylated nitrogen atom, or else (morpholinomethyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

The carboxyl radical(s) of the products of formula (I) can be salified or esterified with various groups known to those skilled in the art, among which mention may be made, by way of non-limiting examples, of the following compounds:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine, among the esterification compounds, alkyl radicals for forming alkoxycarbonyl groups such as, for example, methoxcarbonyl, ethoxycarbonyl, tert-butoxycarbonyl or benzyloxycarbonyl, it being possible for these alkyl radicals to be substituted with radicals chosen, for example, from halogen atoms, hydroxyl radicals, alkoxy radicals, acyl radicals, acyloxy radicals, alkylthio radicals, amino radicals or aryl radicals, for instance in chloromethyl, hydroxypropyl, methoxymethyl, propionyloxymethyl, methylthiomethyl, dimethylaminoethyl, benzyl or phenethyl groups.

The term "esterified carboxyl" is intended, for example, to mean radicals such as alkyloxy-carbonyl radicals, for example methoxycarbonyl, ethoxycarbonyl, propoxycarbonyl, butyloxycarbonyl, tert-butyloxycarbonyl, cyclobutyloxycarbonyl, cyclopentyloxycarbonyl or cyclohexyloxycarbonyl. Mention may also be made of radicals formed with readily cleavable ester residues, such as methoxymethyl or ethoxymethyl radicals; acyloxyalkyl radicals such as pivaloyloxymethyl, pivaloyloxyethyl, acetoxymethyl or acetoxyethyl; alkyloxycarbonyloxy alkyl radicals such as methoxycarbonyloxy methyl or ethyl radicals, isopropyloxycarbonyloxy methyl or ethyl radicals. A list of such ester radicals can be found, for example, in European patent EP 0 034 536.

The term "amidated carboxyl" is intended to mean, for example, radicals of the type —CONR3R4 in which R3 and R4 have the meanings indicated above.

The term "alkylamino radicals" is intended to mean radicals in which the alkyl radical is chosen from the alkyl radicals mentioned above. Preference is given to alkyl radicals containing at most 4 carbon atoms, and mention may, for example, be made of methylamino radicals, ethylamino radicals, propylamino radicals or butylamino radicals, which may be linear or branched.

The term "dialkylamino radical" is intended to mean radicals in which the alkyl radicals, which may be identical or different, are chosen from the alkyl radicals mentioned above. As previously, preference is given to alkyl radicals containing at most 4 carbon atoms, and mention, may, for example, be made of dimethylamino radicals, diethylamino radicals or methylethylamino radicals, which may be linear or branched.

The radicals NR3R4 can also be a heterocycle which may or may not contain an additional hetero atom. Mention may be made of pyrrolyl, imidazolyl, indolyl, piperidyl, morpholinyl and piperazinyl radicals. Piperidinyl, morpholinyl or piperazinyl radicals are preferred.

The term "salified carboxyl" is intended to mean the salts formed, for example, with an equivalent of sodium, of potassium, of lithium, of calcium, of magnesium or of ammonium.

Mention may also be made of the salts formed with organic bases, such as methylamine, propylamine, trimethylamine, diethylamine or triethylamine. The sodium salt is preferred.

When the products of formula (I) comprise an amino radical that can be salified with an acid, it is clearly understood that these acid salts are also part of the invention. Mention may be made of the salts provided with hydrochloric acid or methanesulphonic acid, for example.

The addition salts with inorganic or organic acids of the products of formula (I) can, for example, be the salts formed with hydrochloric acid, hydrobromic acid, hydriodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulphonic acids such as, for example, methanesulphonic acid, ethanesulphonic acid or propanesulphonic acid, alkyldisulphonic acids such as, for example, methanedisulphonic acid or alpha,beta-ethanedisulphonic acid, arylmonosulphonic acids such as benzenesulphonic acid, and aryldisulphonic acids.

It may be recalled that the stereoisomerism can be defined, in its broad sense, as the isomerism of compounds having the same structural formulae but whose various groups are arranged differently in space, such as in particular in monosubstituted cyclohexanes whose substituents may be in the axial or equatorial position, and the various possible rotational conformations of ethane derivatives. However, there is another type of stereoisomerism, due to the different spatial arrangements of fixed substituents, either on double bonds or on rings, which is often referred to as geometrical isomerism or cis-trans isomerism. The term "stereoisomer" is used in the present application in its broadest sense and thus relates to all the compounds indicated above.

In the products of formula (I) as defined above and below, the alkyl, alkenyl, alkynyl, cycloalkyl, heterocycloalkyl, aryl, heteroaryl, aralkyl or heteroaralkyl radicals can be optionally substituted with one or more radicals, which may be identical or different, chosen from halogen atoms; and the radicals: hydroxyl; cycloalkyl containing at most 6 ring members; acyl containing at most 7 carbon atoms; cyano; nitro; free, salified or esterified carboxyl; tetrazolyl; —NH2, —NH(alk), —N(alk)(alk); $SO_2$—NH—CO—NH—alkyl; $SO_2$—NH—CO—NH-phenyl; —C(O)—$NH_2$; —C(O)—NH(alk); —C(O)—N(alk)(alk), —NH—C(O)-(alk), —N(alk)-C(O)-(alk); thienyl; phenyl, alkyl, alkylthio, alkoxy and phenoxy, themselves optionally substituted with one or more radicals chosen from halogen atoms and hydroxyl, alkoxy, alkyl, —NH2, —NH(alk) and —N(alk)(alk) radicals.

More particularly, in the products of formula (I) as defined above and below, the alkyl, alkenyl, alkynyl, cycloalkyl, heterocycloalkyl, aryl, heteroaryl, aralkyl or heteroaralkyl radicals can be optionally substituted with one or more radicals, which may be identical or different, chosen from halogen atoms; and the radicals: hydroxyl; free, salified or esterified carboxyl; —NH2, —NH(alk), —N(alk)(alk); phenyl, alkyl and alkoxy, themselves optionally substituted with one or more radicals chosen from halogen atoms and hydroxyl, alkoxy, alkyl, —NH2, —NH(alk) and —N(alk)(alk) radicals.

Even more particularly, in the products of formula (I) as defined above and below, the alkyl, alkenyl, alkynyl, cycloalkyl, heterocycloalkyl, aryl, heteroaryl, aralkyl or heteroaralkyl radicals can be optionally substituted with one or more radicals, which may be identical or different, chosen from halogen atoms and hydroxyl and alkoxy radicals.

The present invention thus relates in particular to the products of formula (I) as defined above, in which:
A1, A2, A3 and A4, which may be identical or different, are such that A1 and A4, which may be identical or different, are CRa and A2 and A3 are N or CRa,
the substituents n; Ra, R1 and R2 having the meanings indicated above;

said products of formula (I) being in all the possible racemic, enantiomeric and diastereoisomeric isomer forms, and also the addition salts with inorganic and organic acids or with inorganic and organic bases of said products of formula (I).

The present invention thus relates in particular to the products of formula (I) as defined above, in which:
A1, A2, A3 and A4, which may be identical or different, are such that A1 and A4, which may be identical or different, are CRa and A2 and A3 are N or CRa, with Ra being H or OH,
the substituents n; R1 and R2 having the meanings indicated above;

said products of formula (I) being in all the possible racemic, enantiomeric and diastereoisomeric isomer forms, and also the addition salts with inorganic and organic acids or with inorganic and organic bases of said products of formula (I).

The present invention thus relates in particular to the products of formula (I) as defined above, in which:
A1, A2, A3 and A4 are such that A1 and A4 are CH and A2 and A3, which may be identical or different, are N, CH or COH,
the substituents n; R1 and R2 having the meanings indicated above;

said products of formula (I) being in all the possible racemic, enantiomeric and diastereoisomeric isomer forms, and also the addition salts with inorganic and organic acids or with inorganic and organic bases of said products of formula (I).

The present invention thus relates in particular to the products of formula (I) as defined above, in which:
R1 is an oxygen atom or a radical NRb with Rb being H or (CH2)m-heteroaryl, with m=0, 1 or 2,
the substituents A1, A2, A3, A4, n and R2 having the meanings indicated above;

said products of formula (I) being in all the possible racemic, enantiomeric and diastereoisomeric isomer forms, and also the addition salts with inorganic and organic acids or with inorganic and organic bases of said products of formula (I).

When Rb is $(CH_2)$m-heteroaryl, the present invention relates in particular to the values of Rb in which m is 1 and heteroaryl is a pyridyl radical optionally substituted with an amino radical NR3R4 with R3 and R4 as defined above, the other substituents A1, A2, A3, A4, n and R2 having the meanings indicated above;

said products of formula (I) being in all the possible racemic, enantiomeric and diastereoisomeric isomer forms, and also the addition salts with inorganic and organic acids or with inorganic and organic bases of said products of formula (I).

The present invention thus in particular relates to the products of formula (I) as defined above, in which n is 2,
the substituents A1, A2, A3, A4; R1 and R2 having the meanings indicated above;

said products of formula (I) being in all the possible racemic, enantiomeric and diastereoisomeric isomer forms, and also the addition salts with inorganic and organic acids or with inorganic and organic bases of said products of formula (I).

The present invention relates in particular to the products of formula (I) as defined above, in which:
A1, A2 and A4 are CH and A3 is N, CH or COH,
n is the integer 2;
R1 is an oxygen atom;
R2 is H,
said products of formula (I) being in all the possible racemic, enantiomeric and diastereoisomeric isomer forms, and also the addition salts with inorganic and organic acids or with inorganic and organic bases of said products of formula (I).

The present invention relates most particularly to the products of formula (I) as defined above, having the following names:

1-{3-H-imidazo[4,5-c]pyridin-2-yl}-3,4-dihydro-2H-pyrido[2,1-a] isoindole-6-one, 1-{1-H-6-hydroxybenzimidazol-2-yl}-3,4-dihydro-2H-pyrido[2,1-a] isoindole-6-one, said products of formula (I) being in all the possible racemic, enantiomeric and diastereoisomeric isomer forms, and also the addition salts with inorganic and organic acids or with inorganic and organic bases of said products of formula (I).

A subject of the present invention is also processes for preparing the products of formula (I) according to the present invention.

The Synthesis of the 2,3,4,6-tetrahydro-2H-pyrido[2,1-a] isoindole Ring is Described Little in the Literature Some derivatives substituted in the 1-position of this ring, such as those presented below, are known:

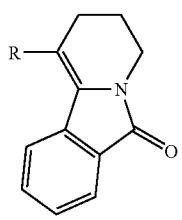

with R=H, CN, CO2Et, PO3Et2, Ph, Ph(substituted), N(Me)Ph, SPh, Salk.

Gourves J.P. et al. (Eur. J. Org. Chem. 1999, 3489) describe a synthesis using an intramolecular cyclization by Horner-Wadworth-Emmons reaction as key step:

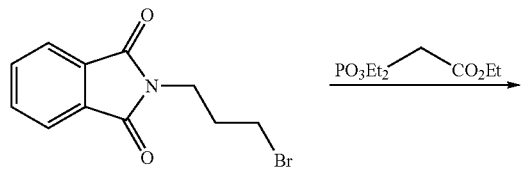

Patent JP 49102699 describes the preparation of 1-phenylthio- and of 1-tert-butylthio-6-oxo-2,3,4,6-tetrahydropyrido[2,1-a]isoindole, in quite a similar manner, but involving a step of photochemical irradiation-induced cyclization of N-(4-phenyl- or 4-tert-butylthiobutyl)phthalimides:

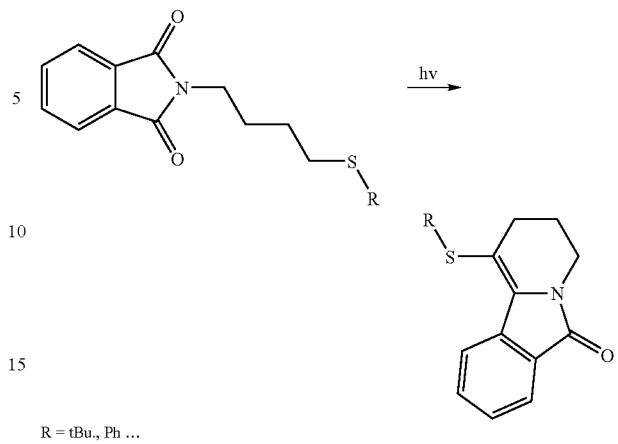

R = tBu., Ph ...

Deok-Chan et al (Tetrahedron Lett. 1996, 37, 2577-80) describe the synthesis of the 6-oxo-2,3,4,6-tetrahydropyrido[2,1-a]isoindole ring by reductive cyclization of N-(4-iodobutylthiobutyl)phthalimide induced by samarium iodide:

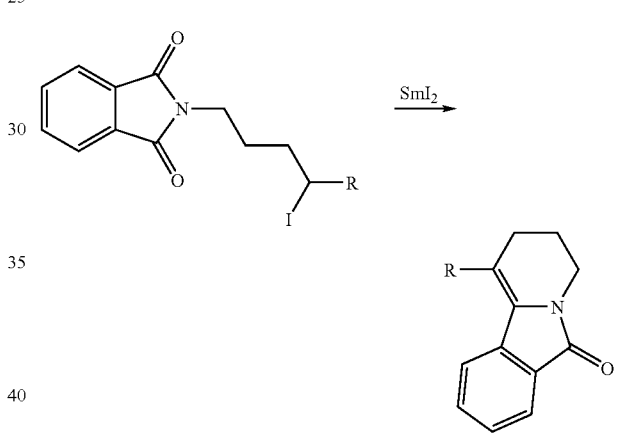

R = H, Me

Earl R. A. and Volhardt P. C. (Heterocycles, 1982, 19, 265-71) describe the synthesis of the 6-oxo-2,3,4,6-tetrahydropyrido[2,1-a]isoindole ring by a retro-ene imino Diels-Alder reaction:

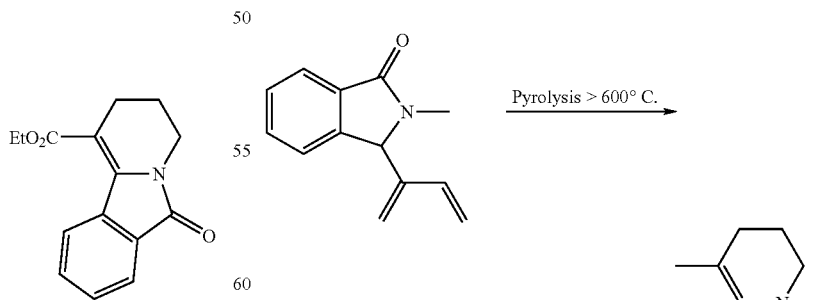

Mazzochi et al (Tetrahedron Lett. 1983, 24,143-46) describe the synthesis of the 6-oxo-2,3,4,6-tetrahydropyrido[2,1-a]isoindole ring by a Paterno-Buchi intramolecular reaction:

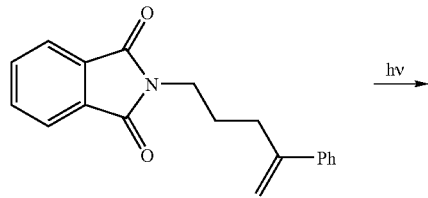

Finally, Malacria M. et al (Organic Lett. 2003, 5, 5095-97) describe the synthesis of the 6-oxo-2,3,4,6-tetrahydropyrido[2,1-a]isoindole ring by a tandem free-radical cyclization reaction:

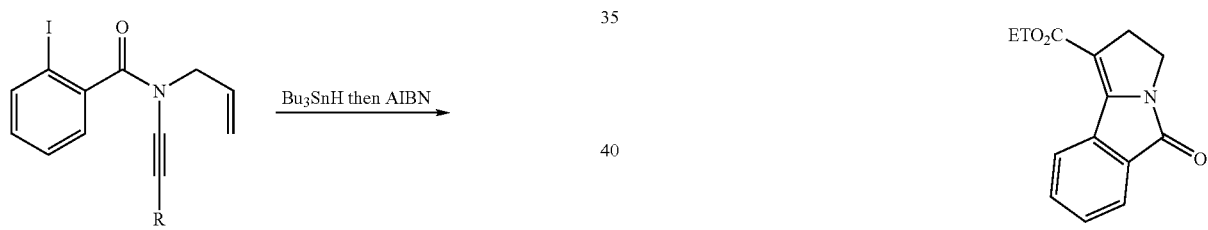

R = H, Me, CO2Et, TMS

The 2,3,4,6-tetrahydro-2H-pyrido[2,1-a]isoindole backbone is also sometimes found in more complex tetracyclic structures such as the merocyanin derivatives described in patent IT671447, the hemiporphyrazine derivatives described in patent SU 178001, or the dyes used as copolymers in the production of synthetic textile fibres, such as those described in patents DE 2128326, BE662237, U.S. Pat. No. 3,221,041 or NL 6504566.

The Synthesis of the 2,5-dihydro-3H-pyrrolo[2,1-a]isoindole Ring is Described Little in the Literature Some derivatives substituted in the 1-position of this ring, such as those present below, are known:

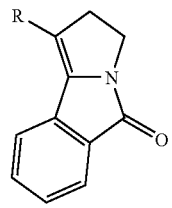

with R=H, CN, CO2Et, CO2Me, Ph, StBu.

Petter R. C. et al (J. Org. Chem. 1990, 55, 3088-3097) describe a synthesis implementing an intramolecular cyclization by Horner-Wadworth-Emmons reaction as key step:

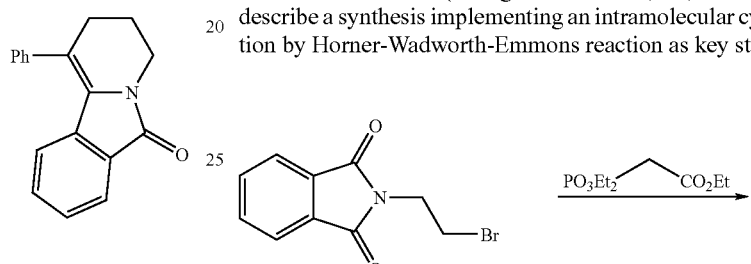

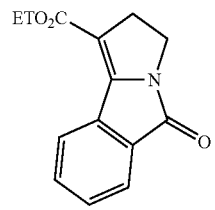

Muchovski et al (Tetrahedron Lett. 1980, 21, 4585-88) describe a synthesis by means of the opening of a triphenylphosphonium salt of a cyclopropanoic ester by a phthalimide:

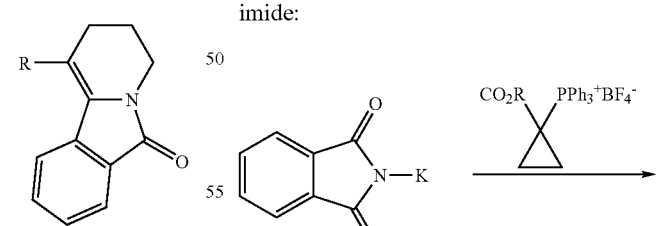

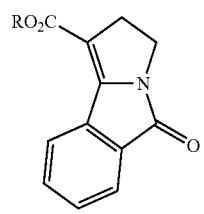

Deok-Chan et al (Tetrahedron Lett. 1996, 37, 2577-80) describe a synthesis by reductive cyclization of N-(4-iodobutylthiobutyl)phthalimide induced by samarium iodide:

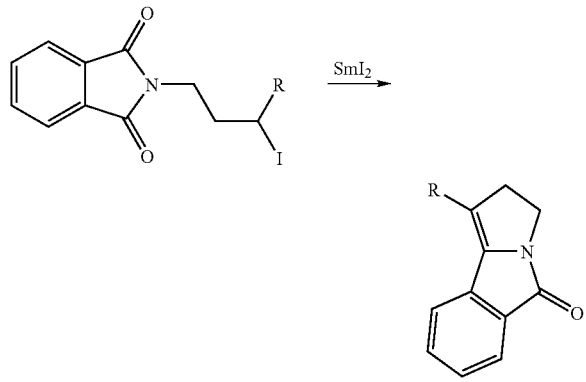

R = H, Me

Yoon et al (J. Amer. Chem. Soc. 1995, 117, 2698-2710) describe a synthesis by cycladdition of an azomethine ylide with an acrylate followed by dehydration of the adduct in an acidic medium:

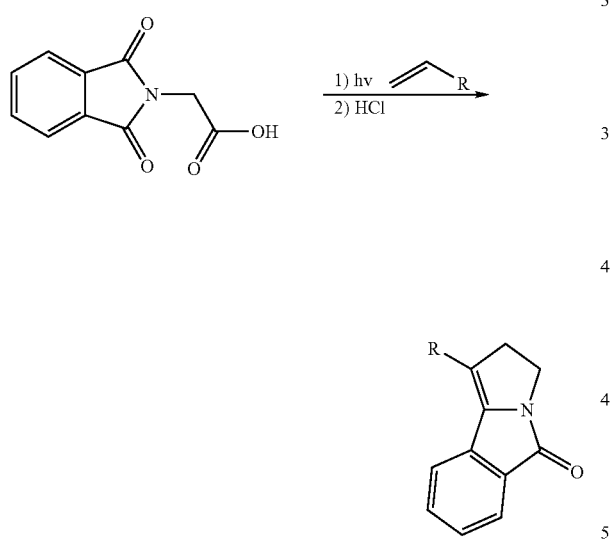

R = CO2Me, CN

Sato et al (Liebigs Ann. Chem. 1985, 1099-1108) describe a synthesis involving a step consisting of cyclization induced by photochemical irradiation of N-(4-phenyl- or 4-tert-butylthiobutyl)phthalimides:

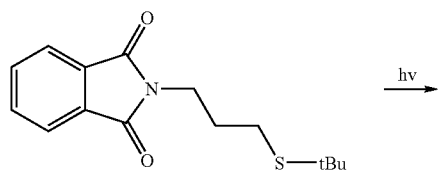

-continued

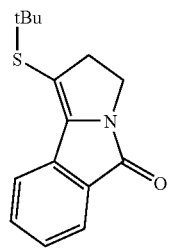

Furthermore, the 2,5-dihydro-3H-pyrrolo[2,1-a]isoindole backbone is found in many tetracyclic compounds.

General Methods of Synthesis

A first original general method, described in general scheme 1, based on the studies above, has been developed and has proved to be particularly advantageous in the context of the present invention, in particular for the synthesis of derivatives of 6-oxo-2,3,4,6-tetrahydropyrido[2,1-a]isoindole type:

Scheme 1

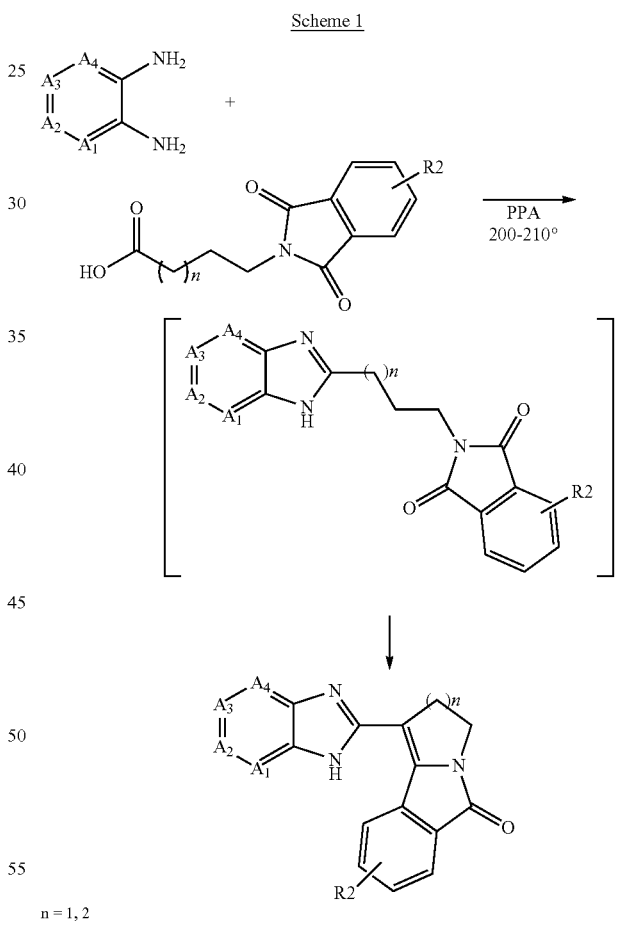

n = 1, 2

The conversion of the radical =O to radicals =R1 as defined in general formula (I) can be carried out according to the general methods known to those skilled in the art, in particular those described in:

Comprehensive Organic Chemistry, by D. Barton et al. (Pergamon Press);

Advanced Organic Chemistry, by J. Marsh (Wiley Interscience).

A general method of synthesis has been developed using 6-oxo-2,3,4,6-tetrahydro-1H-pyrido[2,1-a]isoindole-1-carboxylic acid methyl ester or 6-oxo-2,5-dihydro-3H-pyrrolo[2,1-a]isoindole-1-carboxylic acid methyl ester, by formation of the benzimidazole type ring. It has been found to be particularly advantageous, in the context of the present invention, to carry out the process in 2 successive steps according to scheme 2:

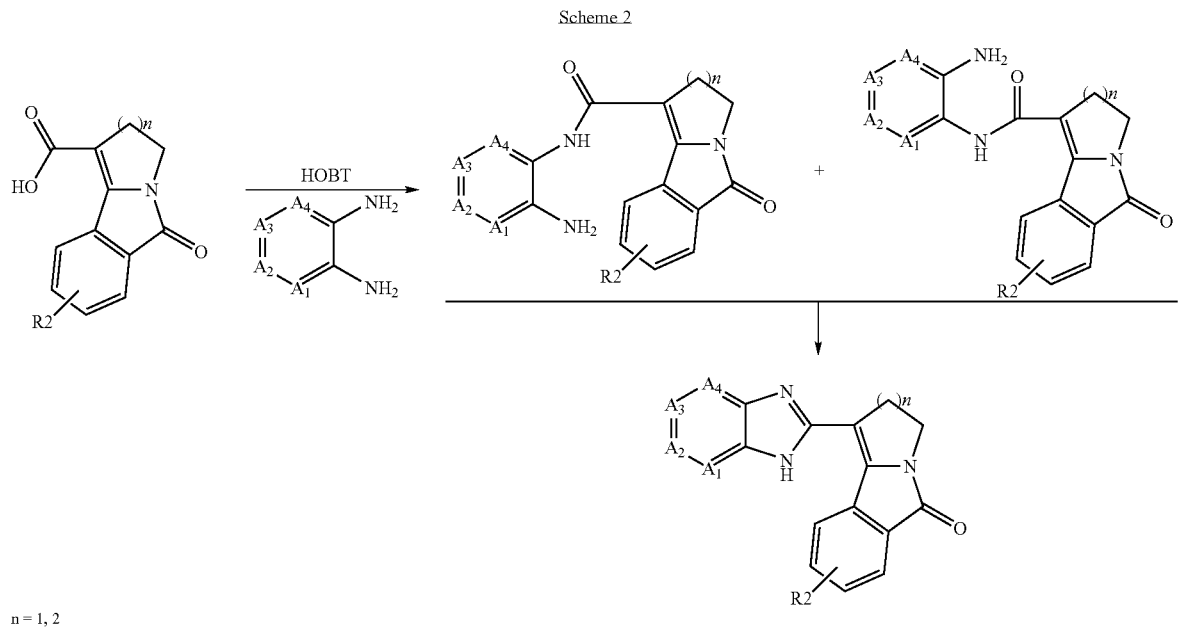

Scheme 2 n = 1, 2

The products that are the subject of the present invention have advantageous pharmacological properties: it has been noted that they in particular have inhibitory properties with respect to the ATPase activity of chaperone proteins. Among these proteins, mention is in particular made of Hsp90.

A subject of the invention is therefore the use, as medicinal products, of the pharmaceutically acceptable products of general formula (I).

A subject of the invention is more particularly the use, as medicinal products, of the products having the following names:

1-{3-H-imidazo[4,5-c]pyridin-2-yl}-3,4-dihydro-2H-pyrido[2,1-a]isoindole-6-one,
1-{1-H-6-hydroxybenzimidazol-2-yl}-3,4-dihydro-2H-pyrido[2,1-a]isoindole-6-one, and also the prodrugs thereof, said products of formula (I) being in all the possible racemic, enantiomeric and diastereoisomeric isomer forms, and also the pharmaceutically acceptable addition salts with inorganic and organic acids or with inorganic and organic bases of said products of formula (I).

The products can be administered parenterally, buccally, perlingually, rectally or topically.

The subject of the invention is also the pharmaceutical compositions, characterized in that they contain, as active ingredient, at least one of the medicinal products of general formula (I).

A subject of the invention is thus the pharmaceutical compositions as defined above, characterized in that they are used as medicinal products, in particular for cancer chemotherapy.

A subject of the invention is thus the pharmaceutical compositions as defined above, also containing active ingredients of other medicinal products for cancer chemotherapy.

These compositions can be provided in the form of injectable solutions or suspensions, tablets, coated tablets, capsules, syrups, suppositories, creams, ointments and lotions. These pharmaceutical forms are prepared according to the usual methods. The active ingredient can be incorporated into excipients normally used in these compositions, such as aqueous or nonaqueous carriers, talc, gum arabic, lactose, starch, magnesium stearate, cocoa butter, fatty substances of animal or plant origin, paraffin derivatives, glycols, various wetting agents, dispersants or emulsifiers, or preserving agents.

The usual dose, that is variable depending on the individual treated and the condition in question, can, for example, be from 10 mg to 500 mg per day in humans, given orally.

The products corresponding to general formula (I) as defined above thus exhibit a substantially inhibitory activity on the Hsp90 chaperone.

A subject of the present invention is thus also the use of products of formula (I) as defined above or of pharmaceutical acceptable salts of said products of formula (I), for preparing a medicinal product for use in preventing or treating a disease characterized by the disturbance of the activity of the Hsp90 protein.

A subject of the present invention is thus the use of products of formula (I) as defined above or of pharmaceutically acceptable salts of said products of formula (I), for preparing medicinal products for use in inhibiting the activity of the Hsp90 protein.

A subject of the present invention is thus the use of products of formula (I) as defined above or of pharmaceutically acceptable salts of said products of formula (I), in which the disease to be prevented or treated is in a mammal. Tests given in the experimental section hereinafter illustrate the inhibitory activity of products of the present invention with respect to such proteins.

A subject of the present invention is thus also the use of products of formula (I) as defined above or of pharmaceutically acceptable salts of said products of formula (I), for preparing a medicinal product for use in treating cancers.

A subject of the present invention is thus also the use of products of formula (I) as defined above or of pharmaceutically acceptable salts of said products of formula (I), in which the disease to be treated is a cancer consisting of solid or liquid tumours.

The properties of the products of general formula (I) of the present invention therefore render them usable as medicinal products, in particular for the treatment of malignant tumours.

Among these cancers, the present invention is most particularly interested in the treatment of solid tumours and in the treatment of cancers resistant to cytotoxic agents.

A subject of the present invention is thus also the use of products of formula (I) as defined above or of pharmaceutically acceptable salts of said products of formula (I), in which the disease to be treated is a cancer resistant to cytotoxic agents.

A subject of the present invention is also the use of products of formula (I) as defined above or of pharmaceutically acceptable salts of said products of formula (I), for preparing a medicinal product for use in treating cancers, among which are lung cancer, breast cancer and ovarian cancer, glioblastomas, chronic myeloid leukaemias, acute lymphoblastic leukaemias, prostate cancer, pancreatic cancer and colon cancer, metastatic melanomas, thyroid tumours and renal carcinomas.

Also among the main potential indications of Hsp90 inhibitors, mention may, in a non-limiting capacity, be made of:

"non-small-cell" lung cancers, breast cancers, ovarian cancers and glioblastomas which overexpress EGF-R or HER2;
chronic myeloid leukaemias which overexpress Bcr-Abl;
acute lymphoblastic leukaemias which overexpress Flt-3;
breast, prostate, lung, pancreatic, colon or ovarian cancers which overexpress Akt;
metastatic melanomas and thyroid tumours which overexpress the mutated form of the B-Raf protein;
androgen-dependent and androgen-independent prostate cancers;
oestrogen-dependent and oestrogen-independent breast cancers;
renal carcinomas which overexpress HIF-la or the mutated c-met protein, etc.

The present invention also relates to the use of products of formula (I) as defined above or of pharmaceutically acceptable salts of said products of formula (I) for preparing a medicinal product for use in cancer chemotherapy. As medicinal products according to the present invention for use in cancer chemotherapy, the products of formula (I) according to the present invention can be used alone or in combination with chemotherapy or radiotherapy, or alternatively in combination with other therapeutic agents.

A subject of the present invention is thus also the use of products of formula (I) as defined above or of pharmaceutically acceptable salts of said products of formula (I), for preparing medicinal products for use in cancer chemotherapy, used alone or in combination.

The present invention thus relates in particular to the pharmaceutical compositions as defined above, also containing active ingredients of other medicinal products for cancer chemotherapy.

Such therapeutic agents can be commonly used antitumour agents.

A subject of the present invention is thus also the use of products of formula (I) as defined above or of pharmaceutically acceptable salts of said products of formula (I), for preparing medicinal products to be used alone or in combination with chemotherapy or radiotherapy, or alternatively in combination with other therapeutic agents.

A subject of the present invention is thus also the use of products of formula (I) as defined above or of pharmaceutically acceptable salts of said products of formula (1), in which the therapeutic agents can be commonly used antitumour agents.

As examples of known protein kinase inhibitors, mention may in particular be made of butyrolactone, flavopiridol, 2-(2-hydroxyethylamino)-6-benzylamino-9-methylpurine, olomucine, Glivec and Iressa.

The products of formula (I) according to the present invention can thus also be advantageously used in combination with antiproliferative agents: by way of examples of such antiproliferative agents, but without, however, being limited to this list, mention may be made of aromatase inhibitors, antioestrogens, topoisomerase I inhibitors, topoisomerase II inhibitors, agents that are active on microtubules, alkylating agents, histone deacetylase inhibitors, farnesyl transferase inhibitors, COX-2 inhibitors, MMP inhibitors, mTOR inhibitors, antineoplastic antimetabolites, platinum compounds, compounds that decrease the activity of protein kinases and also antiangiogenic compounds, gonadorelin agonists, antiandrogens, bengamides, biphophonates and trastuzumab.

By way of examples, mention may be made of antimicrotubule agents such as taxoids, vinca alkaloids, alkylating agents such as cyclophosphamide, DNA-intercalating agents such as cis-platinum, agents that interact with topoisomerase, such as camptothecin and derivatives, anthracyclines such as adriamycin, antimetabolites such as 5-fluorouracil and derivatives and analogues.

The present invention therefore relates to products of formula (I) as protein kinase inhibitors, said products of formula (I) being in all the possible racemic, enantiomeric and diastereoisomeric forms, and also the pharmaceutically acceptable addition salts with inorganic and organic acids or with inorganic and organic bases of said products of formula (I), and also the prodrugs thereof.

The present invention relates particularly to products of formula (I) as defined above as Hsp90 inhibitors, said products of formula (I) being in all the possible racemic, enantiomeric and diastereoisomeric isomer forms, and also the pharmaceutically acceptable addition salts with inorganic or organic acids or with inorganic and organic bases of said products of formula (I), and also the prodrugs thereof.

The products of formula (I) according to the present invention can be prepared by the application or the adaptation of known methods, and in particular of the methods described in the literature, for instance those described by R. C. Larock in: Comprehensive Organic Transformations, VCH publishers, 1989.

In the reactions described hereinafter, it can be necessary to protect reactive functional groups such as, for example, hydroxyl, amino, imino, thio or carboxyl groups, when the latter are desired in the final product but when their participation is not desired in the reactions for the synthesis of the products of formula (I). Use may be made of conventional protective groups in accordance with the usual standard practices, such as those described, for example, by T. W. Greene and P. G. M. Wuts in "Protective Groups in Organic Chemistry" John Wiley and Sons, 1991.

The examples for which the preparation follows illustrate the present invention without, however, limiting it.

EXAMPLES ILLUSTRATING THE INVENTION

Example 1

1-{3-H-imidazo[4,5-c]pyridin-2-yl}-3,4-dihydro-2H-pyrido[2,1-a]-isoindole-6-one 4 g of pyridine-3,4-diamine and 9.5 g of 5-(1,3-dioxo-1,3-dihydroisoindol-2-yl)pentanoic acid are introduced into a 250 ml round-bottomed flask, followed by 45 g of polyphosphoric acid (PPA). The solid mixture is heated to 210° C. in an oil bath. During the reaction, the transient formation of 2-{4-(3H-imidazo[4,5-c]pyridin-2-yl)butyl}isoindole-1,3-dione is noted. After heating for 16 hours, the reaction is complete. After cooling, the reaction mixture is taken up in water. The impurities are eliminated by extraction with ethyl acetate. The aqueous phase is neutralized (pH 7) with 2N sodium hydroxide. The product is recovered after 6 successive extractions with a mixture of ethyl acetate and methanol (9/1 by volume). After purification by flash chromatography silica, elution being carried out with a mixture of dichloromethane and methanol (95/5 by volume), 1.46 g of 1-{3-H-imidazo[4,5-c]pyridin-2-yl}-3,4-dihydro-2H-pyrido[2,1-a]isoindole-6-one are obtained in the form of a white solid, the characteristics of which are as follows:

1H NMR spectrum (400 MHz DMSO-d6): 2.08 (m, 2H); 2.88 (t, J=6.0 Hz, 2H); 3.81 (t, J=6.0 Hz, 2H), 7.54 (m, 2H); 7.60 (d, J=5.5 Hz, 1H); 7.78 (m, 1H); 7.95 (broad m, 1H); 8.34 (d, J=5.5 Hz, 1H); 8.97 (s, 1H); 12.95 (very broad m, 1H).

mass spectrum (E/I): m/z=302 (M+)

Example 2

1-{1-H-6-hydroxybenzimidazol-2-yl}-3,4-dihydro-2H-pyrido[2,1-a]isoindole-6-one

Step 1: 942 mg of 3,4-dihydro-2H-pyrido[2,1-a]isoindole-6-one-1-carboxylic acid methyl ester, which can be obtained according to Eur. J. Org. Chem. 1999, 3489, are dissolved in 10 ml of dioxane, in a 25 ml three-necked flask, and 168 mg of lithium hydroxide monohydrate are added. After stirring for 6 hours at ambient temperature, the dioxane is evaporated off and the product is taken up with 20 ml of water, and then the solution is brought to pH=2 by the addition of a 1M aqueous hydrochloric acid solution. The precipitate formed is filter-dried, washed with water, and then dried in an oven under vacuum at 50° C. 820 mg of 3,4-dihydro-2H-pyrido[2,1-a]isoindole-6-one-1-carboxylic acid are thus obtained in the form of a white powder that is used as it is in the subsequent step.

Step 2: 442.5 mg of 3,4-dihydro-2H-pyrido[2,1-a]isoindole-6-one-1-carboxylic acid are dissolved in 20 ml of dichloromethane, in a 25 ml three-necked flask, and then 400 mg of 1-(3-dimethylaminopropyl)-3-ethylcarbodiimide hydrochloride (EDCI) and 270 mg of 1-hydroxybenzotriazole are added and the mixture is stirred at ambient temperature for 1 hour. After concentration of the solvent under reduced pressure, 10 ml of tetrahydrofuran and 276 mg of 4-methoxybenzene-1,2-diamine are added successively and the mixture is brought to 70° C. for 5 hours. The reaction medium is evaporated off and 680 mg of the mixture of the two regioisomeric amides are thus obtained, which mixture is used as it is in the subsequent step.

Step 3: 118 mg of the mixture of regioisomers obtained above are dissolved in 5 ml of trifluoroacetic acid and 0.5 ml of trifluoroacetic anhydride, in a 100 ml three-necked flask, and the solution is heated at 85° C. for 2.5 hours. After concentration under reduced pressure, the residue is purified by flash chromatography on silica gel, elution being carried out with a mixture of diisopropyl ether and methanol (95/5 by volume). 97 mg of 1-{1-H-6-methoxybenzimidazol-2-yl}-3,4-dihydro-2H-pyrido[2,1-a]isoindole-6-one are thus obtained in the form of a beige powder, the characteristics of which are as follows:

mass spectrum (E/U): m/z=331 (M+)

Step 4: A solution of 61 mg of 1-{1-H-6-methoxybenzimidazol-2-yl}-3,4-dihydro-2H-pyrido[2,1-a]isoindole-6-one in 2 ml of acetic acid and 3 ml of a 48% aqueous hydrobromic acid solution are stirred at ambient temperature for 20 hours in a 25 ml three-necked flask. The reaction medium is poured into 100 ml of water and neutralized with a saturated sodium hydrogen carbonate solution in the presence of 25 ml of dichloromethane. The aqueous phase is re-extracted twice with 20 ml of dichloromethane. The combined organic phases are dried over magnesium sulphate and concentrated under reduced pressure. The crude product is obtained by chromatography on silica gel, elution being carried out with mixtures of dichloromethane and methanol (95/5 then 90/10 by volume); 49 mg of 1-{1-H-6-hydroxybenzimidazol-2-yl}-3,4-dihydro-2H-pyrido[2,1-a]isoindole-6-one are thus obtained in the form of a white foam, the characteristics of which are as follows:

mass spectrum (E/I): m/z=317 (M+).

1H NMR spectrum (400 MHz DMSO-d6): 2.04 (m, 2H); 2.83 (t, J=6.0 Hz, 2H); 3.80 (t, J=6.0 Hz, 2H), 6.74 (broad d, J=8.5 Hz, 1H); 6.90 (broad m, 1H); 7.42 (broad m, 1H); 7.53 (m, 2H); 7.75 (m, 1H); 8.02 (broad m, 1H); 9.22 (broad m, 1H); 12.4 (very broad m, 1H).

Example 3

Pharmaceutical Composition

Tablets corresponding to the following formula were prepared:

| | |
|---|---|
| Product of Example 1 | 0.2 g |
| Excipient for a tablet with a final mass of (details of the excipient: lactose, talc, starch, magnesium stearate). | 1 g |

Biological Assays for Biologically Characterizing the Products of the Invention

The organic phosphate released during the hydrolysis of ATP by the ATPase activity of Hsp82 is quantified by the malachite green method. In the presence of this reagent, formation of the inorganic phosphate-molybdate-malachite green complex occurs, which complex absorbs at a wavelength of 620 nm. The products to be evaluated are incubated in a reaction volume of 30 μl, in the presence of 1 μM Hsp82 and of 250 μpM of substrate (ATP) in a buffer composed of 50 mM Hepes-NaOH (pH 7.5), 1 mM DTT, 5 mM MgCl$_2$ and 50 mM KCl at 37° C. for 60 minutes. In parallel, a range of inorganic phosphate between 1 and 40 μM is prepared in the same buffer. The ATPase activity is subsequently visualized by the addition of 60 μl of the biomol green reagent (Tebu). After incubation at ambient temperature for 20 minutes, the absorbance of the various wells is measured using a microplate reader at 620 nm. The concentration of organic phosphate of each sample is then calculated from the standard curve. The ATPase activity of Hsp82 is expressed as concentration of inorganic phosphate produced in 60 minutes. The effect of the various products tested is expressed as percentage inhibition of the ATPase activity.

The formation of ADP due to the ATPase activity of Hsp82 was used to develop another method for evaluating the enzymatic activity of this enzyme by application of an enzymatic coupling system involving pyruvate kinase (PK) and lactate dehydrogenase (LDH). In this kinetic-type spectrophotometric method, the PK catalyzes the formation of ATP and of pyruvate from phosphoenol pyruvate (PEP) and from the ADP produced by Hsp82. The pyruvate formed, which is a substrate for LDH, is subsequently converted to lactate in the presence of NADH. In this case, the decrease in NADH concentration, measured by the decrease in absorbance at the wavelength of 340 nm, is proportional to the concentration of ADP produced by Hsp82.

The products tested are incubated in a reaction volume of 100 µl of buffer composed of 100 mM Hepes-NaOH (pH 7.5), 5 mM MgCl2, 1 mM DTT, 150 mM KCl, 0.3 mM NADH, 2.5 mM PEP and 250 µM ATP. This mixture is preincubated at 37° C. for 30 minutes before the addition of 3.77 units of LDH and 3.77 units of PK. The reaction is initiated by the addition of the product to be evaluated, at varying concentrations, and of Hsp82, at a concentration of 1 µM. The enzymatic activity of Hsp82 is then measured, continuously, in a microplate reader, at 37° C., at the wavelength of 340 nm. The initial rate of the reaction is obtained by measuring the slope of the tangent at the origin of the curve recorded. The enzymatic activity is expressed in pM of ADP formed per minute. The effect of the various products tested is expressed as percentage inhibition of the ATPase activity according to the coding below:

A: IC50<1 µM
B: 1 µM<IC50<10 µM
C: 10 µM<IC50<100 µM

Table of Results

| Example | Structure | Hsp82 ATPase IC50 µM |
|---|---|---|
| 1 | 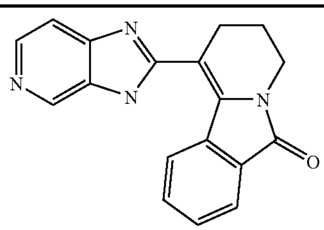 | B |
| 2 | 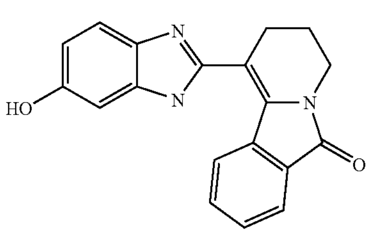 | C |

What is claimed is:
1. A compound of formula (I)

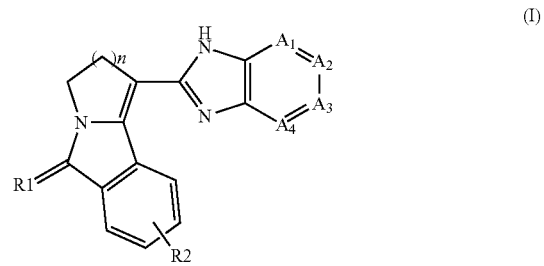

wherein:
  A1, A2, and A4, which may be identical or different, are CRa and R3 is Cra or N;
  n is the integer 2;
  R1 is an oxygen or sulphur atom or a radical NH;
  R2 is independently selected from the group consisting of H, halogen, CF3, nitro, cyano, methyl, ethyl, hydroxyl, mercapto, amino, methylamino and dimethylamino,
  Ra is selected from the group consisting of H, halogen, CF3, hydroxyl, mercapto, nitro, amino, OR3, SR3or NR3R; R3 and R4 are independently chosen from the group consisting of a hydrogen atom, alkyl,
  a racemate, enantiomer, or diastereomer of said compound or an inorganic or organic acid addition salt, or an inorganic or organic base addition salt of said compound, racemate, enantiomer, or diastereomer.

2. A compound according to claim 1 wherein:
A1, A2, A3 and A4, which may be identical or different, are such that A1 A2 and A4, which may be identical or different, are CRa, and A 3 is N or CRa, wherein Ra is H or OH.

3. A compound according to claim 1 wherein:
R1 is an oxygen atom.

4. A compound according to claim 1 wherein:
A1, A2 and A4 are CH, and A3 is N, CH or COH;
n is the integer 2;
R1 is an oxygen atom; and
R2 is H.

5. A compound according to claim 1 which is:
1-{3-H-imidazo[4,5-c]pyridin-2-yl}-3,4-dihydro-2H-pyrido[2,1-a] isoindole-6-one; or 1-{1-H-6-hydroxyberizimidazol-2-yl}-3,4-dihydro-2H-pyrido[2,1-a] isoindole-6-one; or or an inorganic or organic acid addition salt, or an inorganic or organic base addition salt of said compound.

6. A pharmaceutical composition comprising a pharmaceutically effective amount of a compound according to claim 1 and a pharmaceutically acceptable excipient.

7. A pharmaceutical composition according to claim 6, comprising a pharmaceutically effective amount of a compound which is 1-{3-H-imidazo[4,5-c]pyridin-2-yl}-3,4-dihydro-2H-pyrido [2,1-a] isoindole-6-one; or 1-{1-H-6-hydroxybenzimidazol-2-yl}-3,4-dihydro-2H-pyrido[2,1-a] isoindole-6-one; or a an inorganic or organic acid addition salt, or an inorganic or organic base addition salt of said compound; and a pharmaceutically acceptable excipient.

8. A pharmaceutical composition according to claim 6, further comprising at least one other cancer chemotherapeutic agent.

* * * * *